United States Patent
Shi et al.

(10) Patent No.: US 9,012,628 B2
(45) Date of Patent: Apr. 21, 2015

(54) CRYSTALLINE FORM OF ERTAPENEM SODIUM AND PREPARATION METHOD THEREFOR

(75) Inventors: Ying Shi, Shijiazhuang (CN); Kun Li, Shijiazhuang (CN); Xuebin Zhao, Shijiazhuang (CN); Zan Xie, Shijiazhuang (CN); Yuxiu Ma, Shijiazhuang (JP); Jian Lv, Shijiazhuang (CN); Ming Jia, Shijiazhuang (CN)

(73) Assignee: CSPC Zhongqi Pharmaceutical Technology (Shijiazhuang) Co. Ltd., Shijiazhuang (CN)

( * ) Notice: Subject to any disclaimer, the term of this patent is extended or adjusted under 35 U.S.C. 154(b) by 16 days.

(21) Appl. No.: 13/997,957

(22) PCT Filed: Dec. 22, 2011

(86) PCT No.: PCT/CN2011/084430
§ 371 (c)(1),
(2), (4) Date: Jun. 25, 2013

(87) PCT Pub. No.: WO2012/089058
PCT Pub. Date: Jul. 5, 2012

(65) Prior Publication Data
US 2013/0281427 A1    Oct. 24, 2013

(30) Foreign Application Priority Data

Dec. 31, 2010 (CN) .......................... 2010 1 0620554

(51) Int. Cl.
| | | |
|---|---|---|
| C07D 477/20 | (2006.01) | |
| A61K 31/407 | (2006.01) | |
| A61K 9/00 | (2006.01) | |
| A61K 9/19 | (2006.01) | |
| A61K 47/02 | (2006.01) | |

(52) U.S. Cl.
CPC ............ *C07D 477/20* (2013.01); *A61K 9/0019* (2013.01); *A61K 9/19* (2013.01); *A61K 47/02* (2013.01)

(58) Field of Classification Search
USPC ...................................... 540/350; 514/210.12
See application file for complete search history.

(56) References Cited

U.S. PATENT DOCUMENTS

| | | | |
|---|---|---|---|
| 5,652,233 | A | 7/1997 | Betts et al. |
| 6,504,027 | B1 * | 1/2003 | Williams et al. .............. 540/350 |
| 7,022,841 | B2 | 4/2006 | Cvetovich et al. |
| 7,071,330 | B2 | 7/2006 | Williams et al. |
| 7,145,002 | B2 | 12/2006 | Brands et al. |

FOREIGN PATENT DOCUMENTS

| | | |
|---|---|---|
| CN | 1079224 A | 12/1993 |
| CN | 1486318 A | 3/2004 |
| CN | 1602312 A | 3/2005 |
| CN | 1752090 A | 3/2006 |
| WO | 99/45010 A1 | 9/1999 |
| WO | 03/026572 A2 | 4/2003 |
| WO | 03/027067 A2 | 4/2003 |
| WO | 2008/062279 A2 | 5/2008 |
| WO | 2009/150630 A2 | 12/2009 |

OTHER PUBLICATIONS

Zhang et al., "Synthesis of carbapenem antibiotic ertapenem," Journal of China Pharmaceutical University 38(4): 305-310, 2007. (with English Abstract).

Brands et al., Prosecution History for, "Crystalline Forms of Carbapenem Antibiotics and Methods of Preparation," U.S. Patent No. 7,145,002, Issued Dec. 5, 2006, 65 pages.

* cited by examiner

*Primary Examiner* — Robert D. Harlan
(74) *Attorney, Agent, or Firm* — Seed IP Law Group PLLC

(57) ABSTRACT

Provided is a crystalline form E of ertapenem sodium. Further provided is a method for preparing a crystalline form E of ertapenem sodium, characterized by using an aqueous ertapenem sodium solution at a low concentration as a raw material. The crystalline form E can be easily filtered and dried, the properties in the drying process are stable, and the purity of the crystal is high and can be up to 98.5% or higher.

12 Claims, 1 Drawing Sheet

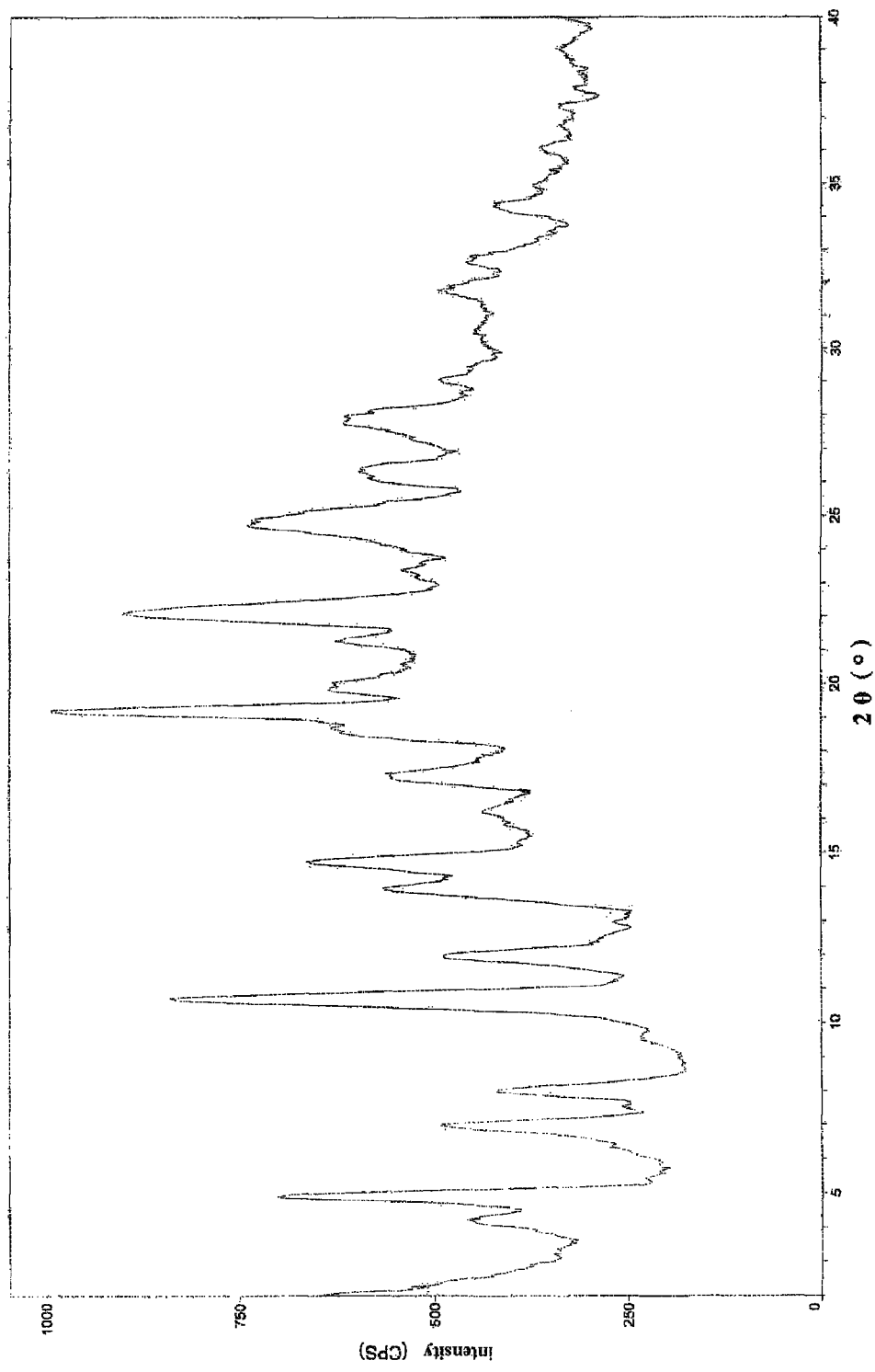

CRYSTALLINE FORM OF ERTAPENEM SODIUM AND PREPARATION METHOD THEREFOR

FIELD OF THE INVENTION

The present invention relates to the studies on crystalline form of ertapenem sodium, specifically to a crystalline form E of ertapenem sodium and the preparation method therefor.

BACKGROUND OF THE INVENTION

Ertapenem sodium has the structure of formula I, which chemical name is (1R,5S,6S,8R,2S*,4S*)-2-[2-[(3-carboxyphenyl)carbamoyl]-pyrrolidinyl-4-thio]-6-(1-hydroxyethyl)-1-methylcarbapenem-3-carboxylic acid monosodium salt. Ertapenem sodium is a novel broad-spectrum carbapenem antibiotic jointly developed by Merck & Co. (U.S.) and AstraZeneca, which has good antibacterial activities against gram-positive and gram-negative aerobic and anaerobic bacteria.

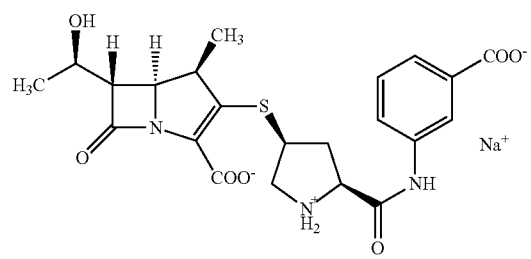

Polymorphism is an important nature of a compound, and is generally present in the majority of chemical drugs. Substance in different crystalline form has important influence on the stability, uniformity, bioavailability, and formulation, etc. Ertapenem sodium is poor in stability, and is highly sensitive to heat, acid, etc. In order to reduce the degredation of the product, and to improve the quality of formulation product, research workers have performed enormous studies on the crystalline forms of ertapenem sodium, and various crystalline forms of ertapenem sodium and the preparation methods therefor have been disclosed in the prior art.

For example, WO03026572 discloses crystalline form A and crystalline form B of ertapenem sodium and the preparation method therefor. The crystalline form A has major diffraction peaks at about 4.8°, 6.7°, 10.5°, 11.7°, 13.6°, 14.4°, 16.0°, 17.2°, 18.4°, 19.7°, 20.8°, 21.6°, 22.1°, 23.1°, 24.1°, 26.1°, 26.6°, 27.0°, 27.4°, 28.6°, and 31.1° in the X-ray diffraction spectrum presented by 2θ angle. The crystalline form B has major diffraction peaks at about 4.8°, 6.8°, 7.8°, 10.4°, 11.8°, 13.6°, 14.4°, 15.2°, 17.3°, 18.5°, 19.0°, 19.7°, 20.9°, 21.9°, 23.1°, 24.1°, 24.5°, 26.1°, 26.5°, 26.9°, 27.7°, 28.7°, 30.0°, 31.1°, and 32.2° in the X-ray diffraction spectrum presented by 2θ angle.

The method for preparing crystalline form A comprises: a) adding 1-propanol to an aqueous solution containing ertapenem of formula II and III and/or salt forms thereof; b) cooling the solution to below −5° C.; c) adjusting the pH to between about 6 and about 5 utilizing an acid; d) crystallizing by adding to the solution from about 0.5 to about 3 volumes of methanol relative to the aqueous solution volume, and from about 0.5 to about 3 volumes of 1-propanol relative to the aqueous solution volume; and e) isolating to obtain the crystalline form A of ertapenem sodium.

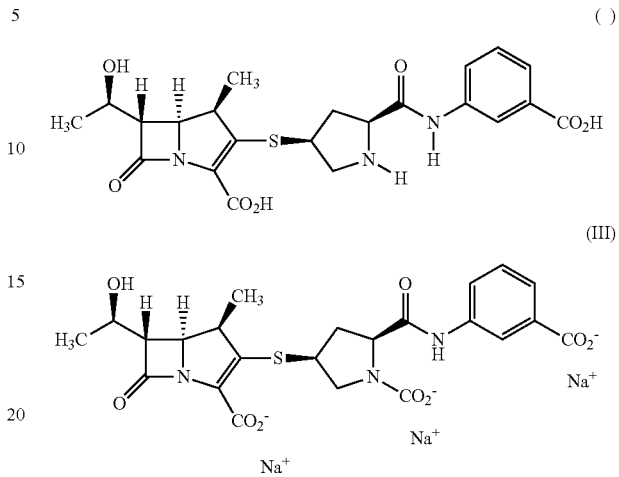

The method for preparing crystalline form B comprises the steps of: washing the crystalline form A of ertapenem sodium with a mixture of water and 2-propanol to give the crystalline form B, wherein said mixture contains about 5% to about 25% water (v/v).

In addition, WO03027067 discloses a crystalline form C of ertapenem sodium. In the method disclosed by this patent, the crystalline form C of ertapenem sodium is isolated and obtained after washing the above-mentioned crystalline form A or crystalline form B of ertapenem sodium with a aqueous solvent of ethyl acetate, acetone, or a mixture thereof. The crystalline form C of the compound has major diffraction peaks at about 4.8°, 6.8°, 7.8°, 10.7°, 11.8°, 13.7°, 14.6°, 17.3°, 18.6°, 19.14°, 19.9°, 21.0°, 22.1°, 24.2°, 26.1°, 27.9°, 28.7°, 31.3°, and 32.5° in the X-ray diffraction spectrum presented by 2θ angle.

The methods for preparing crystalline form A, crystalline form B, and crystalline form C of ertapenem sodium all have the following disadvantages: in the above-mentioned methods, when ertapenem sodium is crystalized, the concentrations for the crystalization solutions of ertapenem sodium are all required to be above 100 mg/ml. Due to the fact that ertapenem sodium is easily to be degraded and polymerized, conventional concentration and nanofiltration will cause substantive degradation of the product. Therefore, due to the excessive concentration of ertapenem sodium solution, both the purity and the chroma of the crystal are difficult to meet the requirements. In addition, large amount of solvent is also introduced in the above-mentioned method, which is not conducive to the environmental protection.

WO2009150630 discloses a crystalline form D of ertapenem sodium. This crystalline form D has major diffraction peaks at about 4.44°, 5.26°, 7.44°, 8.12°, 10.98°, 12.74°, 19.28°, 22.93°, 23.51°, 25.07°, and 30.15° in the X-ray diffraction spectrum presented by 2θ angle. The method for preparing crytalline form D comprises the following steps: a) treating ertapenem sodium with water and methanol; b) treating the solution obtained in step a) with 1-propanol; c) stirring the mixture obtained in step b) at a temperature of about 0° C. or below 0° C., for the precipitation of solid; d) treating the solid obtained in step c) with acetone, to obtain the crystalline form D of ertapenem sodium. The disadvantages of the crystalline form D of ertapenem sodium are that the crystallization properties are poor, the particle is small, and filtration by suction is difficult.

In addition to the above-mentioned various crystalline forms product of ertapenem sodium disclosed in the prior art, several methods for preparing amorphous products of ertapetanem sodium have also been disclosed in the prior art, for example:

In CN1752090A, acetone and propanol are added into a reaction system of ertapenem sodium after extraction, and insolubles are removed, and the product is precipitated by means of evaporative crystallization, which is then washed by 95% ethanol and methyl acetate, and purified, to obtain an amorphous product of ertapenem sodium.

For another example, a method for preparing ertapenem sodium solid is recited in "Synthesis of carbapenem antibiotic ertapenem" by ZHANG Yi-feng (Journal of China Pharmaceutical University, 2007, 38(4): 305-310), which comprises the following steps: the reaction liquid of ertapenem sodium is filtered, then the filtrate is extracted with dichloromethane, and the aqueous layer is concentrated under reduced pressure to remove organic solvent, then purified by CHP-20P resin, and then lyophilized to obtain white powder of ertapenem sodium, which shows an amorphous product after examined by X-ray.

The main disadvantages of the above-mentioned amorphous product of ertapenem sodium are: poor stability, low purity, and that it is difficult for the color grade to meet the requirements.

SUMMARY OF THE INVENTION

The technical problem to be solved by the present invention is to provide a crystalline form E of ertapenem sodium. Compared with the prior art, in the process for preparing the crystalline form E of ertapenem sodium provided by the present invention, the concentration of ertapenem sodium solution required is low, and the crystalline form E obtained is of high purity, and has good stability.

In order to solve the above-mentioned technical problems, the present invention provides a crystalline form E of ertapenem sodium shown in formula (I),

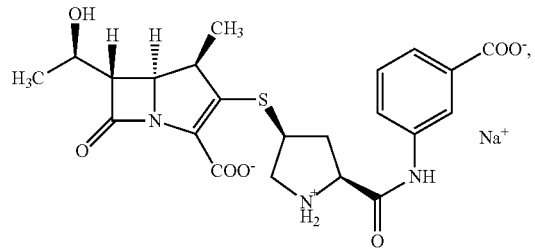

(I)

Using CuKα radiation, the X-ray diffraction spectrum of the crystalline form has major diffraction peaks at Bragg angles 2θ (°) of 4.220, 4.900, 6.980, 8.000, 10.720, 11.960, 13.958, 14.740, 17.319, 18.641, 19.200, 22.060, 24.780, 26.299, and 27.920±0.2°.

The present invention further provides a method for preparing the crystalline form E of ertapenem sodium, comprising the steps of:

a) providing an aqueous solution of ertapenem sodium at a concentration of 40~100 mg/ml;

b) adjusting the pH value of the aqueous solution of ertapenem sodium with an acid to 5.3~5.6, at a condition of 0~20° C.;

c) adding dropwise methanol and 1-propanol to the solution obtained in step b), until the volume ratio of water:methanol:1-propanol is 1:0.5~2:0.25~1.5, then cooling to −10~−5° C. and allowing stand;

d) adding dropwise methanol and 1-propanol to the solution obtained in step c), until the volume ratio of water:methanol:1-propanol is 1:0.8~3:0.8~3.5, then cooling to −30~−10° C. and precipitating crystal, to obtain the crystalline form E of ertapenem sodium.

Preferably, the concentration of the aqueous solution of ertapenem sodium in step a) is 50~90 mg/ml.

Preferably, the acid in step b) is one or more selected from the group consisting of formic acid, acetic acid, propanoic acid and hydrochloric acid, preferably acetic acid.

Preferably, the pH value of the aqueous solution of ertapenem sodium in step b) is adjusted to 5.4~5.5 with an acid.

Preferably, the temperature for precipitating crystal in step d) is −25~−15° C.

Preferably, in step c), methanol and 1-propanol are added dropwise to the solution obtained in step b), until the volume ratio of water:methanol:1-propanol is 1:0.8~1.5:0.4~1.

Preferably, in step d), methanol and 1-propanol are added dropwise to the solution obtained in step c), until the volume ratio of water:methanol:1-propanol is 1:1~2.5:1~3.

Preferably, the method further comprises a step of adding dropwise seed crystal to the solution obtained after adding methanol and 1-propanol in step c).

The present invention further provides use of the crystalline form E of ertapenem sodium in the manufacture of a medicament for treating infection.

The present invention further provides a pharmaceutical composition, comprising the crystalline form E of ertapenem sodium according to the technical solutions mentioned above. The pharmaceutical composition is preferably a lyophilized powder for injection.

The present invention provides a crystalline form E of ertapenem sodium. The crystalline form E provided by the present invention is easily to be filtered, dried, and is stable in nature during the drying process, and the purity of the crystal is high and can reach more than 98.5%. Moreover, in the process for preparing the crystalline form E of ertapenem sodium provided by the present invention, due to the lower concentrations of ertapenem sodium solution employed, the difficulty and energy consumption for concentrating is reduced, which is conducive to the industrial production.

DESCRIPTION OF THE DRAWINGS

FIG. 1 is the X-ray diffraction spectrum of the crystalline form E of ertapenem sodium prepared in the Example 1 of the present invention.

DETAILED EMBODIMENTS

The present invention discloses a crystalline form E of ertapenem sodium. Using CuKα radiation, the X-ray diffraction spectrum of the crystalline form has major diffraction peaks at Bragg angles 2θ (°) of 4.220, 4.900, 6.980, 8.000, 10.720, 11.960, 13.958, 14.740, 17.319, 18.641, 19.200, 22.060, 24.780, 26.299, and 27.920. As will be appreciated by those skilled in the art that the diffraction peaks of crystalline form according to the present invention are not limited to those appeared at the above-mentioned 2θ angles, and further comprise diffraction peaks appeared within the above-mentioned 2θ angles±0.2° due to the experimental error and other factors, which should also be within the protection scope of the present invention. The concentration of the aqueous solution of ertapenem sodium mentioned herein is the ratio of the solute mass to the solvent volume.

The present invention discloses a method for preparing crystalline form E of the ertapenem sodium, comprising:

a) providing an aqueous solution of ertapenem sodium at a concentration of 40~100 mg/ml;

b) adjusting the pH value of the aqueous solution of ertapenem sodium with an acid to 5.3~5.6 at a condition of 0~20° C.;

c) adding dropwise methanol and 1-propanol to the solution obtained in step b), until the volume ratio of water:methanol:1-propanol is 1:0.5~2:0.25~1.5, then cooling to −10~−5° C. and allowing stand;

d) adding dropwise methanol and 1-propanol to the solution obtained in step c), until the volume ratio of water:methanol:1-propanol is 1:0.8~3:0.8~3.5, then cooling to −30~−10° C. and precipitating the crystal, to obtain the crystalline form E of ertapenem sodium.

According to the present invention, in step a), crude ertapenem sodium can be dissolved in water, to obtain an aqueous solution at a concentration of 40~100 mg/ml. For the crude ertapenem sodium, it can be prepared according to the methods disclosed in the prior art, specific examples are the preparation methods disclosed in CN93101472.7, CN02803742.1, CN9880609.1, CN200510030660.5, U.S. Pat. No. 6,504,027, WO03026572, WO2008062279, "Synthesis of carbapenem antibiotic ertapenem" by ZHANG Yi-feng (Journal of China Pharmaceutical University, 2007, 38(4): 305-310), etc, but are not limited thereto. The contents of the above-mentioned documents are incorporated herein by reference. The concentration of the aqueous solution of ertapenem sodium in step a) is preferably 50~90 mg/ml.

According to the present invention, in step b), the pH value of the aqueous solution of ertapenem sodium is adjusted with an acid to 5.3~5.6, preferably to 5.4~5.5, at a condition of preferably 2~18° C., more preferably 5~15° C. Said acid is preferably one or more selected from the group consisting of formic acid, acetic acid, propanoic acid and hydrochloric acid, more preferably acetic acid.

According to the present invention, in step c), it is preferable to add dropwise methanol and 1-propanol to the solution obtained in step b), until the volume ratio of water:methanol:1-propanol is 1:0.8~1.5:0.4~1, then cooling to −10~−5° C. and allowing stand. Before allowing stand, it is preferable to add seed crystal, then allow stand, and the solution is stirred until it turns turbid. For the time for standing, it is preferably 5~30 minutes.

In step d), it is preferable to keep the temperature in step c) unchanged, then methanol and 1-propanol are added dropwise, until the volume ratio of water:methanol:1-propanol is 1:0.8~3:0.8~3.5, preferably 1:1~2.5:1~3, then cooling to −30~−10° C., more preferably −25~−15° C., then stirred for 1~10 h and the crystal is precipitated to obtain the crystalline form E of ertapenem sodium.

According to the present invention, after step d), it can further comprises the step of isolating the crystalline form E of ertapenem sodium. For the isolating method, it can be filtrating and other methods well known by a person skilled in the art, such as filtrating and then drying, but not limited thereto.

The present invention further provides use of the crystalline form E of ertapenem sodium in the manufacture of a medicament for treating infection.

The present invention further provides a pharmaceutical composition, comprising the crystalline form E of ertapenem sodium provided by the present invention as active ingredient. The pharmaceutical composition is preferably a lyophilized powder for injection.

In comparison with the prior art, the crystalline form E of ertapenem sodium provided by the present invention is easily to be filtered, dried, and is stable in nature during the drying process, and the purity of the crystal is high and can reach more than 98.5%. Moreover, in the process for preparing the crystalline form E of ertapenem sodium provided by the present invention, due to the low concentration of ertapenem sodium solution employed, the difficulty and energy consumption for concentrating is reduced, which is conducive to the industrial production.

In order to further understand the present invention, the novel crystalline form of ertapenem sodium provided by the present invention is described in conjunction with examples, however, the protection scope of the present invention is not limited to the following examples.

The X-ray diffraction spectra of the samples in the following examples were determined under the following conditions:

Instrument: Rigaku D/max-2550 powder X-ray diffractometer, Japan;

Conditions: CuKα radiation, graphite monochromator, tube voltage 40 kV, tube current 40 mA, 2θ scanning range 2~40°, scanning speed 8°/minute, step width 0.02°.

EXAMPLE 1

Preparation of Crystalline Form E of Ertapenem Sodium, According to the Following Steps a) 10 g crude ertapenem sodium was taken and dissolved in water to formulate a solution of 80 mg/ml;

b) the pH value of the solution obtained in step a) was adjusted to 5.5 with hydrochloric acid at 0° C.;

c) methanol and 1-propanol were added dropwise to the solution obtained in step b), until the volume ratio of water:methanol:1-propanol is 1:1:0.6, cooled to −8° C., and seed crystal was added and allowed stand for 30 min, and stirred until the solution was turbid;

d) the temperature of the solution obtained in step c) was kept unchange, and methanol and 1-propanol were further added to the solution, until the molar ratio of water:methanol:1-propanol was 1:1.2:1.5, and cooled to −18° C., stirred for 5 h, and the crystal was precipitated; and e) 8.5 g solid was obtained by filtering and drying.

The prepared solid was taken and tested by HPLC, and the purity of ertapenem sodium was 99.3%;

The prepared solid was additionally taken and tested by X-ray, and the data of the X-ray diffraction spectrum are shown in Table 1:

TABLE 1 the X-ray diffraction spectrum of the crystalline form E of ertapenem sodium prepared according to Example 1

| 2θ Angle (°) | Interplanar crystal spacing d (Å) | Relative height (%) |
|---|---|---|
| 4.220 | 20.9215 | 27.3 |
| 4.900 | 18.0179 | 71.2 |
| 6.980 | 12.6541 | 43.8 |
| 8.000 | 11.0423 | 34.8 |
| 10.720 | 8.2461 | 100.0 |

TABLE 1-continued the X-ray diffraction spectrum of the crystalline form
E of ertapenem sodium prepared according to Example 1

| 2θ Angle (°) | Interplanar crystal spacing d (Å) | Relative height (%) |
|---|---|---|
| 11.960 | 7.3936 | 38.9 |
| 13.958 | 6.3394 | 27.3 |
| 14.740 | 6.0048 | 42.3 |
| 16.239 | 5.4539 | 9.4 |
| 17.319 | 5.1159 | 28.3 |
| 18.641 | 4.7562 | 26.8 |
| 19.200 | 4.6189 | 79.8 |
| 20.039 | 4.4273 | 14.3 |
| 21.279 | 4.1720 | 14.0 |
| 22.060 | 4.0260 | 64.0 |
| 24.780 | 3.5900 | 43.4 |
| 26.299 | 3.3859 | 20.7 |
| 27.920 | 3.1929 | 25.4 |
| 28.963 | 3.0803 | 6.9 |

EXAMPLES 2~6

The crystalline form E of ertapenem sodium was prepared under different technological conditions, and the detailed technological parameters are shown in Table 2:

TABLE 2 the technological parameters in Examples 2-5

| Step | Conditions | Example 2 | Example 3 | Example 4 | Example 5 | Example 6 |
|---|---|---|---|---|---|---|
| a) | Solution concentration mg/ml | 40 | 50 | 70 | 90 | 100 |
|  | Temperature ° C. | 18° C. | 5° C. | 12° C. | 8° C. | 20° C. |
| b) | pH Value | 5.6 | 5.5 | 5.3 | 5.5 | 5.4 |
|  | Acid | Acetic acid | Propionic acid | Formic acid | Hydrochloric acid | Acetic acid |
| c) | Volume ratio of water:methanol:1-propanol | 1:2:1.5 | 1:1.5:1 | 1:1.2:0.8 | 1:0.8:0.4 | 1:0.5:0.25 |
|  | Temperature ° C. | −5° C. | −9° C. | −10° C. | −6° C. | −8° C. |
|  | Standing time | 30 min | 20 min | 10 min | 10 min | 5 min |
| d) | Volume ratio of water:methanol:1-propanol | 1:3:3.5 | 1:2.5:3 | 1:1.5:2 | 1:1:1.2 | 1:0.8:0.8 |
|  | Cooling temperature | −25° C. | −22° C. | −20° C. | −18° C. | −15° C. |
|  | Stirring time | 10 h | 8 h | 5 h | 3 h | 1 h |

COMPARATIVE EXAMPLES 1~2

The crystalline form E of ertapenem sodium was prepared under different technological conditions, and the detailed technological parameters are shown in Table 3:

TABLE 3 the technological parameters in Comparative Examples 1-2

| Step | Conditions | Comparative example 1 | Comparative example 2 |
|---|---|---|---|
| a) | Solution concentration mg/ml | 30 | 110 |
|  | Temperature ° C. | 2° C. | 10° C. |
| b) | pH Value | 5.5 | 5.5 |
|  | Acid | Formic acid | Hydrochloric acid |
|  | Volume ratio of water:methanol:1-propanol | 1:2.5:2 | 1:0.4:0.25 |
| c) | Temperature ° C. | −10° C. | −6° C. |
|  | Standing time | 20 min | 10 min |
|  | Volume ratio of water:methanol:1-propanol | 1:3.5:4 | 1:0.5:0.6 |
| d) | Cooling temperature | −25° C. | −15° C. |
|  | Stirring time | 3 h | 1 h |

The product weight, yield, HPLC purity, and crystalline form of the Comparative Examples 1~2 were determined respectively, and the results are shown in Table 4:

TABLE 4 the results of Examples 2-6 and Comparative Examples 1-2

| No. | Product weight (g) | Yield (%) | HPLC Purity (%) | Crystalline characteristics |
|---|---|---|---|---|
| Example 2 | 4.3 | 43 | 98.5 | Crystalline form E |
| Example 3 | 7.5 | 75 | 99.0 | Crystalline form E |
| Example 4 | 8.3 | 83 | 99.3 | Crystalline form E |
| Example 5 | 8.6 | 86 | 99.0 | Crystalline form E |
| Example 6 | 8.8 | 88 | 98.7 | Crystalline form E |
| Comparative example 1 | No crystal precipitated | — | — | — |
| Comparative example 2 | 9.0 | 87 | 98.5 | Mixed crystalline form |

The results in Table 4 show that when the concentration of the ertapenem sodium solution was within the range of 40~100 mg/ml and under the condition of the present invention, the crystalline form E of ertapenem sodium can be obtained. The sample recovery rate increased with the increasing of the crystalization concentration of ertapenem sodium; the crystals were not easily to be precipitated when the concentration of ertapenem sodium solution was lower than 40 mg/ml, and when it was higher than 100 mg/ml, the crystalline form of ertapenem sodium obtained was different from the crystalline form E.

EXAMPLE 7

Comparative tests for stability of the crystalline form E and other crystalline forms.

Crystalline form A and crystalline form B of ertapenem sodium were prepared according to the methods disclosed in WO03026572, crystalline form C of ertapenem sodium was prepared according to the method disclosed in WO03027067, crystalline form D of ertapenem sodium was prepared according to the method disclosed in WO2009150630, and amorphous product of ertapenem sodium was prepared according the method disclosed in CN1752090A.

The above-mentioned crystalline forms A, B, C, D, the amorphous solid of ertapenem sodium, and the crystalline form E prepared according to Example 1 were stored for 1 year under refrigerating at 6° C. and freezing at −20° C., and were sampled at month 1, month 3, month 6, month 9, and month 12, respectively, and the total impurity and content of the reserved samples were tested, and the specific data are shown in Table 5:

EXAMPLE 8

Lyophilized Powder of Ertapenem Sodium

Formula:

| | |
|---|---|
| Sample of Example 1 | 1.046 g |
| Sodium bicarbonate | 175 mg |
| Sodium hydroxide | 40 mg |
| Water for injection | q.s. |

The preparation procedure for the formula is as the follows:

First, sodium bicarbonate and sodium hydroxide in the amount of the formula were weighed and dissolved in water for injection, and cooled to below 5° C. in an ice bath, and the sample of Example 1 in the amount of the formula was added and dissolved, and the pH value was adjusted to 7.5 using sodium hydroxide solution, then the product was obtained by filtration and lyophilization.

The above examples described are only for the purpose of better understanding of the method of the present invention and the core idea thereof. It should be indicated that the present invention can also be improved and modified by those skilled in the art without departing from the principle of the present invention, and these improvements and modifications also fall within the protection scope of the claims of the present invention.

The above description of the disclosed examples enables a person skilled in the art to realize or apply the present invention. Various modifications to these examples are obvious to a

TABLE 5 the results of performances of the crystalline form E and the crystalline forms A, B, C, D, and the amorphous product after preserving

| | | Storage condition | | | | | | | | | |
|---|---|---|---|---|---|---|---|---|---|---|---|
| | | Refrigerating 6° C. | | | | | Freezing −20° C. | | | | |
| | | Sampling time | | | | | | | | | |
| | | month 0 | month 3 | month 6 | month 9 | month 12 | month 0 | month 3 | month 6 | month 9 | month 12 |
| Crystalline form E | Total impurity (%) | 0.8 | 1.3 | 1.6 | 2.1 | 3.2 | 0.8 | 0.8 | 0.8 | 0.8 | 0.8 |
| | Content (%) | 99.1 | 98.5 | 98.1 | 97.5 | 96.8 | 99.1 | 99.0 | 99.1 | 99.0 | 98.9 |
| Amorphous | Total impurity (%) | 1.2 | 2.1 | 5.3 | 7.1 | 9.3 | 1.2 | 1.2 | 1.3 | 1.5 | 1.7 |
| | Content (%) | 98.5 | 97.9 | 94.5 | 92.3 | 90.1 | 98.5 | 98.4 | 98.5 | 98.2 | 98.1 |
| Crystalline form A | Total impurity (%) | 0.7 | 1.2 | 1.5 | 2.0 | 3.0 | 0.7 | 0.7 | 0.7 | 0.7 | 0.7 |
| | Content (%) | 99.2 | 98.6 | 98.1 | 97.6 | 96.9 | 99.2 | 99.2 | 99.1 | 99.2 | 99.1 |
| Crystalline form B | Total impurity (%) | 0.8 | 1.4 | 1.7 | 2.1 | 3.3 | 0.8 | 0.8 | 0.9 | 0.8 | 0.9 |
| | Content (%) | 99.1 | 98.3 | 98.0 | 97.5 | 96.6 | 99.1 | 99.1 | 99.0 | 99.0 | 98.9 |
| Crystalline form C | Total impurity (%) | 0.8 | 1.1 | 1.4 | 1.9 | 3.0 | 0.8 | 0.8 | 0.8 | 0.8 | 0.8 |
| | Content (%) | 99.2 | 98.7 | 98.2 | 97.8 | 96.9 | 99.2 | 99.2 | 99.1 | 99.2 | 99.2 |
| Crystalline form D | Total impurity (%) | 1.0 | 1.9 | 3.1 | 4.6 | 6.5 | 1.0 | 1.1 | 1.1 | 1.2 | 1.2 |
| | Content (%) | 98.8 | 98.0 | 96.8 | 94.7 | 93.2 | 98.8 | 98.7 | 98.7 | 98.6 | 98.5 |

It can be seen from the results in Table 5 that the crystalline form E, and the crystalline forms A, B, C of the ertapenem sodium have comparable stability, which is more stable than the amorphous product and the crystalline form D.

person skilled in the art, and the general principles defined herein can be realized in other examples, without departing from the spirit and scope of the present invention. Therefore, the present invention will not be limited to these examples

The invention claimed is:

1. A crystalline form E of ertapenem sodium of formula (I),

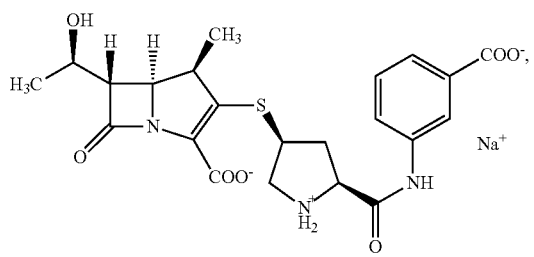

characterized in that, using CuKα radiation, the X-ray diffraction spectrum of the crystalline form has major diffraction peaks at Bragg angles 2θ (°) of 4.220, 4.900, 6.980, 8.000, 10.720, 11.960, 13.958, 14.740, 17.319, 18.641, 19.200, 22.060, 24.780, 26.299, and 27.920±0.2°.

2. A method for preparing the crystalline form E of ertapenem sodium according to claim 1, characterized in that, the method comprises the steps of:
   a) providing an aqueous solution of ertapenem sodium at a concentration of 40~100 mg/ml;
   b) adjusting the pH value of the aqueous solution of ertapenem sodium with an acid to 5.3~5.6, at a condition of 0~20° C.;
   c) adding methanol and 1-propanol dropwise to the solution obtained in step b), until the volume ratio of water:methanol:1-propanol is 1:0.5~2:0.25~1.5, then cooling to −10~−5° C. and allowing stand;
   d) adding methanol and 1-propanol dropwise to the solution obtained in step c), until the volume ratio of water:methanol:1-propanol is 1:0.8~3:0.8~3.5, then cooling to −30~−10° C. and precipitating crystal, to obtain the crystalline form E of ertapenem sodium.

3. The preparation method according to claim 2, characterized in that, the concentration of the aqueous solution of ertapenem sodium in step a) is 50~90 mg/ml.

4. The preparation method according to claim 2, characterized in that, the acid in step b) is one or more selected from the group consisting of formic acid, acetic acid, propanoic acid and hydrochloric acid.

5. The preparation method according to claim 2, characterized in that, the pH value of the aqueous solution of ertapenem sodium in step b) is adjusted to 5.4~5.5 with an acid.

6. The preparation method according to claim 2, characterized in that, the temperature for precipitating crystal in step d) is −25~−15° C.

7. The preparation method according to claim 2, characterized in that, in step c), methanol and 1-propanol are added dropwise to the solution obtained in step b), until the volume ratio of water:methanol:1-propanol is 1:0.8~1.5:0.4~1.

8. The preparation method according to claim 2, characterized in that, in step d), methanol and 1-propanol are added dropwise to the solution obtained in step c), until the volume ratio of water:methanol:1-propanol is 1:1~2.5:1~3.

9. The preparation method according to claim 2, characterized in that, the method further comprises a step of adding seed crystal to the solution obtained after adding dropwise methanol and 1-propanol in step c).

10. A method for treating infection comprising administering the crystalline form E of ertapenem sodium according to claim 1 to a subject in need thereof.

11. A pharmaceutical composition, characterized in that, the composition comprises the crystalline form E of ertapenem sodium according to claim 1.

12. The pharmaceutical composition according to claim 11, which is a lyophilized powder for injection.

* * * * *